United States Patent [19]

Schalkowsky et al.

[11] 4,350,186
[45] Sep. 21, 1982

[54] GRAVIMETRIC DILUTER

[75] Inventors: Samuel Schalkowsky, Chevy Chase, Md.; Donald Whitley, Bingley, England

[73] Assignee: Spinal Systems Inc., Cincinnati, Ohio

[21] Appl. No.: 232,531

[22] Filed: Feb. 9, 1981

[51] Int. Cl.³ ............................................. B65B 3/28
[52] U.S. Cl. .................................... 141/83; 141/102; 177/70
[58] Field of Search ..................... 141/1, 83, 100, 102, 141/130, 192, 392; 177/70

[56] References Cited

U.S. PATENT DOCUMENTS

| | | | |
|---|---|---|---|
| 3,254,728 | 6/1966 | Aguadro et al. | 177/15 |
| 3,263,761 | 8/1966 | Boadle et al. | 177/70 |
| 3,398,689 | 8/1968 | Allington | 417/331 |
| 3,516,506 | 6/1970 | Furlong | 177/164 |
| 3,528,518 | 9/1970 | Mayer | 177/70 |
| 3,805,141 | 4/1974 | Pompa, Jr. et al. | 321/11 |
| 3,959,636 | 5/1976 | Johnson et al. | 177/70 X |
| 4,222,448 | 9/1980 | Sunkle et al. | 177/70 X |

*Primary Examiner*—Frederick R. Schmidt
*Attorney, Agent, or Firm*—Donald E. Stout

[57] ABSTRACT

An apparatus for making dilutions of a sample with a diluent to a predetermined dilution factor f by weight of the diluent is disclosed. A scale with TARE capability produces an output signal of the weight W of a sample within a container less the weight of the container. A dilution factor control is provided for setting the predetermined dilution factor f. Means are provided for calculating and storing the value TW=W/f which is the total weight of the sample plus the weight of the diluent which is required to dilute the sample to the predetermined dilution factor f. A pump is connected between a reservoir of diluent and the container for the sample for pumping the amount of diluent into the container which is required to dilute the sample to the predetermined weight dilution factor f. The scale provides a continuous output of the weight W of the sample plus diluent in the container at any instant in time. Means are provided for calculating when TW−W=0. In one embodiment, the flow of diluent to the container is stopped by the stopping of the pump when TW−W=0. In another embodiment, the flow of diluent to the container is stopped by closing a pair of valves located between the pump and the container when TW−W=0.

7 Claims, 4 Drawing Figures

GRAVIMETRIC DILUTER

CROSS REFERENCE TO RELATED APPLICATION

Reference is made to application Ser. No. 232,525, entitled Gravimetric Diluter, which was filed on the same date as the present application. That application, which is assigned to the assignee of the present application and names Jeptha E. Campbell and James E. Gilchrist as inventors, discloses and claims a gravimetric diluter which utilizes a pump and a pair of valves to control the flow of diluent into a container to make dilutions by weight to a dilution factor f.

BACKGROUND OF THE INVENTION

The invention relates to apparatus for making dilutions of samples of any weight with a diluent to a predetermined weight percentage of diluent.

DESCRIPTION OF THE PRIOR ART

In the fields of microbiology, biochemistry and chemistry it is often necessary to dilute liquid or solid samples with a diluent to a predetermined concentration by weight. In the case of solid samples, the liquid diluent may be used to make a slurry of the solid in the liquid. Bacterial density in solid food or fruit juice samples is determined by analysis of dilutions of these samples. In certain areas such as clinical laboratories or quality control laboratories it is necessary to make dilutions of large numbers of samples. While it is possible to manually dilute samples with diluents to a predetermined percentage by weight or volume, the amount of time required can be great where high accuracy or large numbers of dilutions are required.

Automatic counting and packaging systems are known. In these systems the number of items which are packaged is determined by entering the total weight of the package of items into a microprocessor control and dividing that quantity by the average weight per item to determine the number of items.

Systems are known which make weight measurements of individual ingredients for making concrete or other substances which require a precise weight ratio of the ingredients to make a satisfactory composite mix of the ingredients. These systems are programmable to permit an operator to make a predetermined mixture of, for example, 100 pounds of ingredient A, 200 pounds of ingredient B and 300 pounds of ingredient C. Unlike the present invention, these systems do not make automatic dilutions of a first ingredient of unmeasured weight to a predetermined percentage by weight of a second ingredient.

Pumping systems are known which simultaneously control the pumping of two or more liquids in a predetermined volumetric ratio. Examples of use of such systems are in the field of chromatography, the mixing of two grades of hydrocarbons such as gasoline or oil and in the field of chemical processing. These systems do not make a dilution of a sample of an unknown weight with a diluent to achieve a predetermined weight percentage of diluent in the sample.

SUMMARY OF THE INVENTION

The invention is an apparatus for diluting liquid or solid samples to a predetermined concentration by weight of a diluent. The invention has means for measuring the weight W of a sample within a container less the weight of the container; means for specifying a predetermined dilution factor f by weight of a diluent in a sample; means for calculating TW=W/f; means for calculating TW-W; fluid conducting means disposed between a reservoir of diluent and the container for permitting the diluent to flow from the reservoir to the container for the purpose of diluting a sample within the container to the predetermined concentration by weight of diluent f; and means responsive to the means for calculating TW-W for controlling the flow of diluent between a reservoir and the container to cause diluent to flow between the container and the reservoir when TW>W and to stop the flow of diluent when TW=W. The means for controlling may be a peristaltic pump.

DESCRIPTION OF THE EMBODIMENTS

Figure 1:
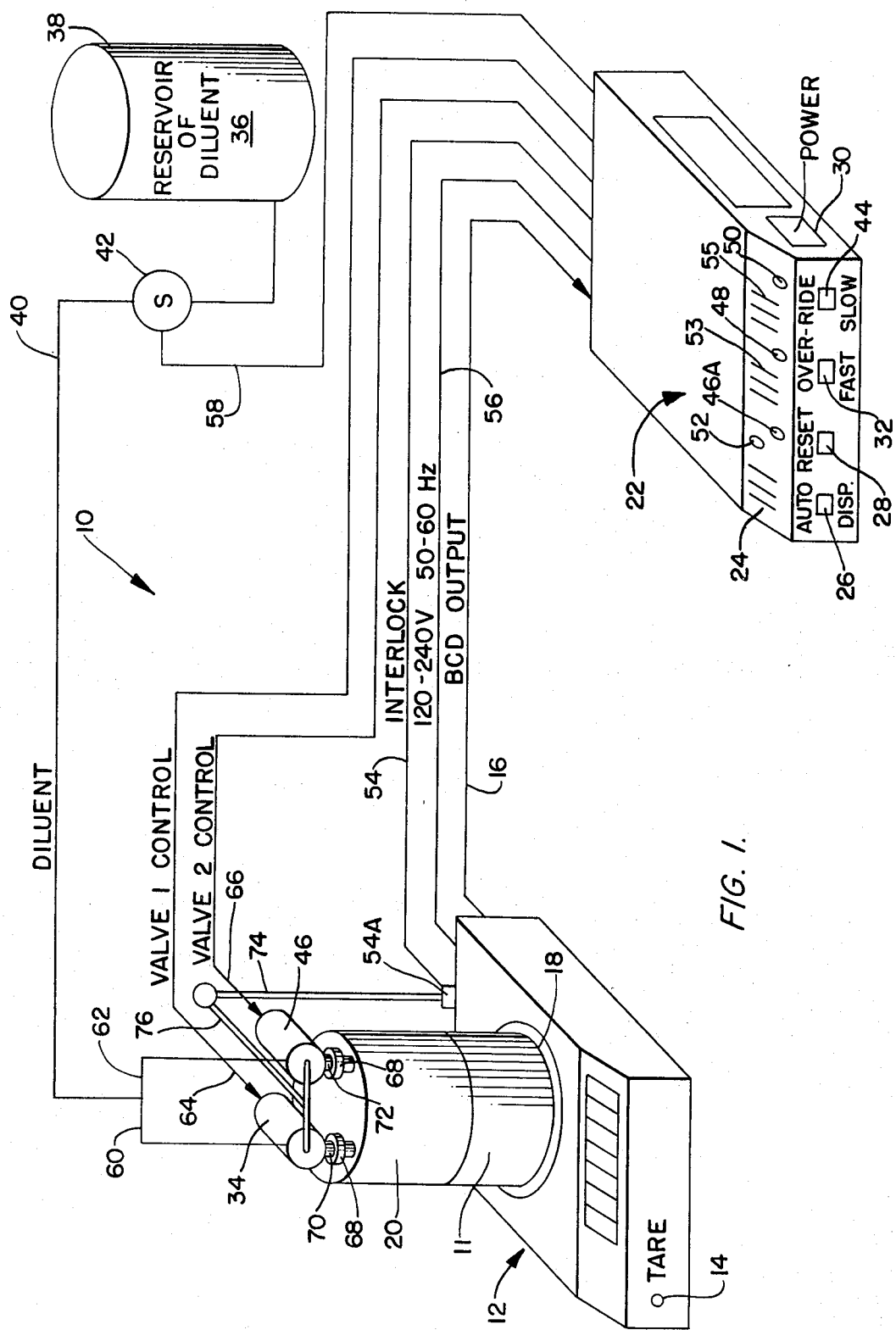
FIG. 1 is a system schematic of one embodiment of the present invention.

FIG. 1 is a general system schematic of the present invention 10 which functions to automatically dilute a sample 11 contained within a container 20 to a predetermined weight dilution factor f of a diluent 36. In accordance with the invention, dilutions of samples 11 are made without requiring measurement of the sample weight prior to placement in the container 20. The dilutions made by the present invention are by weight percentage of the diluent in the sample 11. The dilution factor f of the present invention is defined by the equation:

$$f = \frac{\text{weight of sample}}{\text{weight of diluent} + \text{weight of sample}}$$

For example, a 100 gram solution of ethanol which has been diluted with 100 grams of water is diluted to a weight dilution factor f=0.5 which equals a 50% dilution by weight of diluent. In accordance with the invention, a scale 12 with a TARE control 14 is provided which has an output line 16 on which is continually produced a signal of the weight placed on the pan 18 in binary coded decimal (BCD) format. In accordance with the invention, the TARE control 14 is activated to produce a zero weight BCD output signal on line 16 when the pan 18 has a container 20 resting on it within which a sample 11 will be placed which is to be diluted by diluent 36. Scales are commercially available with TARE controls which produce a BCD output which may be used in the present invention. A suitable commercially available scale having TARE capability and a BCD output which may be used with the present invention is a model PS15 which is manufactured by the Mettler Instrument Corporation of Hightstown, N.J.

The controller 22 of the present invention includes a plurality of controls which include a dilution factor selector control 24, an automatic dispenser switch 26, a manual reset switch 28, an "on"-"off" power switch 30, a rapid manual dispenser switch 32 which is used to manually open a first rapid dispense valve 34 to the flow of diluent 36 from reservoir 38 through conduit 40, under the power of pump 42, a slow dispense switch 44 which is used to manually open a second valve 46 to the flow of diluent 36 from reservoir 38 through conduit 40 under the power of pump 42, a ready light 46A, an excessive sample indicator light 48, an insufficient sample indicator light 50, a power on indicator light 52, maximum weight control 53 and minimum weight control 55. The maximum weight control 53 specifies the maximum weight of sample plus diluent which is permissible for the dilution of a sample to a specified dilution factor f. The minimum weight control 55 specifies the minimum weight of sample plus diluent which is permissible for the dilution of a sample to a specified dilution factor f. The rapid manual dispense switch 32 and the slow manual dispense switch 44 may be used to manually override the automatic control of valves 34 and 46 by the controller 22 to permit selective flow control of diluent into container 20. The first valve 34 has a rated flow rate for a given pressure which is 10 times greater than the flow rate of the second valve 46. The controller 22 has an interlock line 54 which is coupled to a switch 54A and attached to the chassis of the scale 12 which allows valves 34 and 46 attached to the horizontal member 76 to operate when the stanchion 74 is rotated so that switch 54A is closed and valve 34 and valve 46 are over the container 20, a power line 56 which provides suitable electrical power for the scale 12 and a pump activation line 58 which controls the activation of pump 42 for pumping diluent 36 from reservoir 38 through conduit 40, through either the first valve 34 or the second valve 46 into container 20 in a manner to be hereinafter described. The power line for the controller 22 has been omitted. The conduit 40 contains a T section having a input which is coupled to the pump 42 and first and second outputs 60 and 62 which are respectively connected to the first and second valves 34 and 46. Valve control line 64 is connected between the controller 22 and the first valve 34 for selectively controlling the flow of diluent 36 from the pump 42 through the first valve in a manner to be hereinafter explained in conjunction with FIGS. 2 and 3. Valve control line 66 is connected between the controller 22 and the second valve 46 for selectively controlling the flow of diluent 36 from the pump 42 through the second valve 46 in a manner to be hereinafter explained in conjunction with FIGS. 2 and 3. The valves 34 and 46 may have solenoids which are activated under the control of activation signals from the controller 22 over control lines 64 and 66. Valves 34 and 46 may be model V5 valves sold by Skinner Precision Industries, Inc. of New Britain, Conn. Bacterial filters 68 may be coupled between the outputs 70 and 72 of the first and second valves 34 and 46 to filter the diluent 36 prior to discharge into container 20. The valves 34 and 46 are supported above container 20 by a metallic stanchion 74 and a horizontal member 76.

Figure 2:
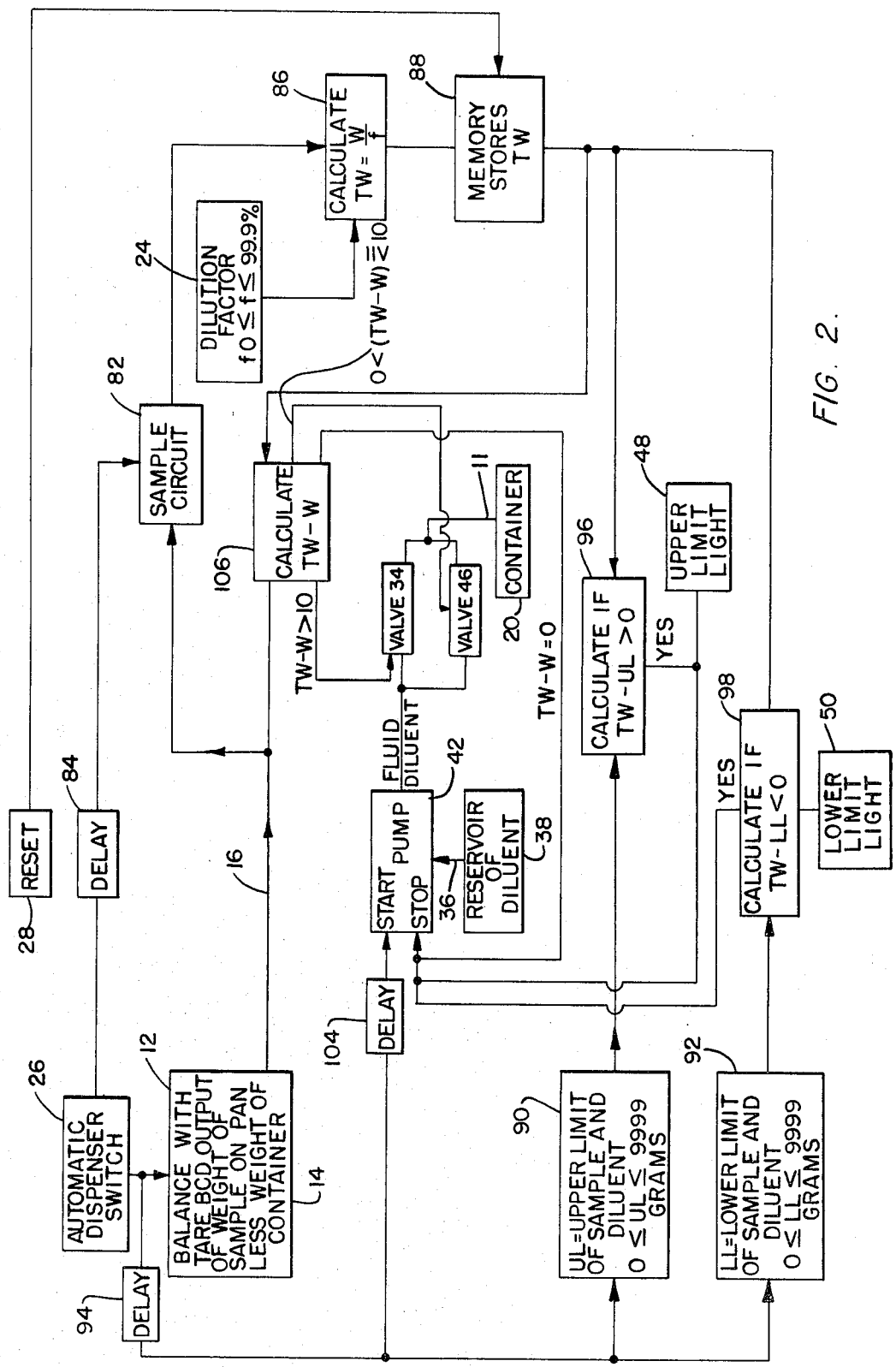
FIG. 2 is a detailed schematic of a control for the embodiment of the present invention illustrated in FIG. 1.

FIG. 2 illustrates a detailed electrical schematic of an embodiment of the invention. It should be understood that the embodiment of FIG. 2 uses digital storage and computation techniques. However, it should also be understood that the present invention may be implemented with equal facility as an analog system. As described in conjunction with FIG. 1, the scale 12 produces a BCD output of the weight on the pan 18 on line 80. The TARE control 14 is activated after the container 20 is placed on the scale 12 but prior to the introduction of a sample 11 which is to be diluted to a predetermined dilution factor f specified by the dilution factor selector control 24. The automatic dispense switch 26, which is depressed after the TARE control 14 is activated and the sample 11 to be diluted with the previously set dilution factor f has been placed in the container 20, causes scale 12 to start to produce a BCD output of the weight of the sample plus diluent in the container 20 on line 16. The BCD output from scale 12 on line 16 is coupled to a sample circuit 82 of any conventional design that samples the BCD output of the weight of the sample 11 prior to the introduction of any diluent. The sample circuit 82 only couples the BCD output from the scale 12 to the means for calculating 86 when the signal from delay 84 is high. The time at which the BCD output is sampled by sample circuit 82 is controlled by the delay 84 which may be a one shot multivibrator or other suitable electrical delay, that produces a high level output signal for a short time interval after the automatic dispense switch is depressed. The time delay produced by the delay 84 need only be sufficient to permit the BCD output of the sample 11 to appear on line 16 after the depressing of the automatic dispense switch 26. The output of the sample circuit 82, is coupled to the means for calculating 86 which calculates TW=W/f where W equals the weight of the sample to be diluted and f equals the weight dilution factor f specified by the dilution factor selector control 24. Since the sample circuit 82 only couples the BCD weight of the sample 11 in the container 20 to be diluted to the means for calculating 86, for a short time interval after depressing the automatic dispense switch 26 during which the output from delay 84 sample circuit is high, the weight represented by the calculated weight TW is equal to the combined weight of the sample and diluent which will be present in the container 20 when the sample has been diluted by the diluent by the weight dilution factor f. The dilution factor selector control 24 may be a combination of a potentiometer, amplifier and analog to digital converter. The circuitry required to convert the analog input f varying such that $0 < f < 0.999$ into a digital format is conventional and forms no part of the present invention. The output TW from the means for calculating 86 is stored in a memory 88 of conventional design which is resettable by the manual reset switch 28. The depressing of the automatic dispense switch 26 also causes digital output signals to be produced from the maximum weight limit control 90 and the minimum weight limit control 92 after a time delay produced by delay circuit 94. The maximum and minimum weight limits, UL and LL of sample plus diluent, are set before depressing of the automatic dispense switch 26. The setting of the maximum and minimum weight limits may be by means of DIP switches or other suitable analog or digital inputs. In the preferred embodiment, the maximum and minimum weight limits may vary between $0 < LL$, $UL < 9999$ grams. The time delay circuit 94 may be a one shot multivibrator of the same type as delay 84. The delay produced by delay 94 is longer than that produced by delay 84 in order to insure that the calculated weight TW has been calculated and stored prior to the output of the maximum and minimum weights from controls 90 and 92 respectively. The output from the maximum weight control 90 is coupled to a means for calculating 96 if $TW - UL > 0$. The output from the minimum weight control 92 is coupled to a means for calculating 98 if $TW - LL < 0$. The output from the means for calculating 96 and 98 are coupled to the stop input of the pump 42 which immediately disables the pump if the calculated weight TW is greater than the specified maximum weight UL from the maximum weight limit control 90 or the specified minimum weight LL from the minimum weight limit control 92. If either condition is present, the system is shut down and an appropriate excessive sample indicator light 48 or an insufficient sample indicator light 50 is lit. If the calculated weight TW does not fall outside the specified maximum and minimum weight limits, the activation of the pump after the expiration of an additional delay produced by delay 104 occurs. The additional delay 104 insures that the pump does not start after the depression of the automatic dispense switch 26 for the case where the calculated weight TW for a dilution would fall outside the maximum and minimum weight limits specified by controls 90 and 92. In the meantime, the scale 12 starts to continually produce a BCD output of the weight of sample 11 plus diluent 36 in the container 20. The BCD output is coupled to a means for calculating 106 the quantity $TW-W$. The means for calculating 106 determines if the quantity $TW-W$ is greater than 10. If $TW-W$ is greater than 10, a control signal is applied by the means for calculating 106 to the first valve 34 to cause diluent to flow only through valve 34 at the highest flow rate. The means for calculating 106 also determines if the quantity $TW-W$ is greater than one but equal to or less than 10. If $1 < TW - W < 10$, a control signal is applied by the means for calculating 106 to the second valve 46 to permit diluent to flow from the reservoir 38 through the pump 42, conduit 40 and the second valve 46 to the container 20. When the control signal is applied to the second valve 46 to only permit diluent to flow through the second valve, the control signal is removed from the first valve 34 to cause it to close. The relative rated flow rates of the first valve 34 and the second valve 46 permit rapid filling of the container 20 to a combined weight of sample plus diluent to within 10 grams of the quantity TW and thereafter slower filling until $TW - W = 1$. When the means for calculating 106 determines that $TW - W = 1$, a pulsating signal is applied to valve 46 to turn on the valve for 0.2 seconds and then to turn off the valve for 1.8 seconds. The pulsating control signal is repeatedly applied to valve 46 until $TW - W = 0$. The purpose of pulsating the valve 46 "on" and "off" when $0 < TW - W < 1$ is to permit the inherent lag in the production of the BCD output signal from the scale 12 on line 16 to not be a factor in shutting off the flow of diluent when $TW - W = 0$. Otherwise overshoot in the amount of diluent added to the sample could occur. When $TW - W$ equals zero, the means for calculating 106 produces an output signal which closes the second valve 46 to prevent further fluid flow through the second valve into the container 20 and shuts off the pump 42. At this instant in time, the dilution of the sample has been completed to a predetermined weight dilution factor f.

Figure 3:
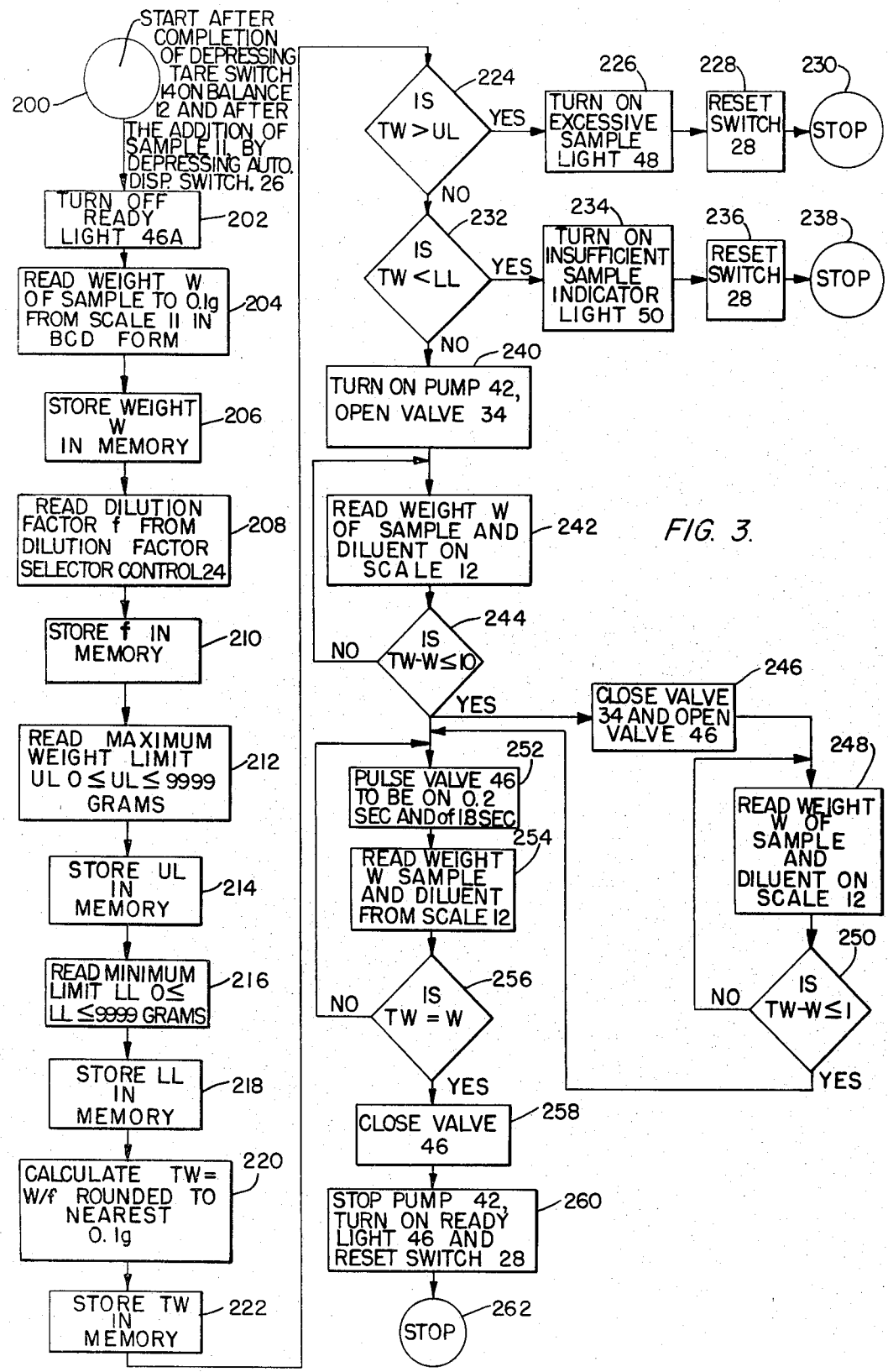
FIG. 3 is a flow chart of the preferred form of a microprocessor control for the embodiment of FIG. 1.

FIG. 3 illustrates a flow chart of the preferred form of implementation of the controller 22 for the invention which utilizes a microprocessor to control the system operation. At the starting point 200 of the microprocessor control program, it is assumed the following sequence of events has occurred: maximum and minimum weights UL and LL of samples and diluent have been entered; the dilution factor f has been set; the power has been turned on; a sample container 20 has been placed on the pan 18; the TARE control 14 has been depressed, a sample 11 has been placed in the container 20; and the automatic dispense switch 26 has been depressed. The program proceeds to block 202 where the ready light on the controller is turned off to signify entry into a dilution of a sample. The program proceeds to block 204 where the weight W of the sample to 0.1 g in BCD format is read from the scale 12. The program proceeds to block 206 where the weight W is stored in memory. The program then proceeds to block 208 where the dilution factor f is read from the dilution input factor control 24 within the controller 22. The program then proceeds to block 210 where the dilution factor f is stored in memory. The program then proceeds to block 212 where the maximum weight limit UL of the sample and diluent is read from the maximum weight control 53 in the controller 22. The range of the maximum weight limit is $0 < UL < 9999$ grams. The program then proceeds to block 214 where the maximum weight UL is stored in memory. The program then proceeds to block 216 where the minimum weight limit LL of sample and diluent is read from the minimum weight control 55 in the controller 22. The range of the minimum weight limit is $0 < LL < 9999$ grams. The program proceeds to block 218 where the minimum weight LL is stored in memory. The program then proceeds to block 220 where the calculated weight $TW = W/f$ is calculated and rounded to the nearest 0.1 g. The program then proceeds to block 222 where TW is stored in memory. The program then proceeds to the decision point 224 where a determination is made if $TW > UL$. If the answer is "yes" the program branches to block 226 where an over weight light 48 in the controller 22 is turned on to indicate that the weight of the sample plus the diluent for achieving the previously set dilution factor f is greater than the specified maximum weight which has been set with the maximum weight control 53. The program then proceeds to block 228 where the memory elements are reset with switch 28 in the controller 22 to prepare the system for another dilution. The program then proceeds to stopping point 230 which terminates all activity in the program. If the answer is "no" at decision point 224, the program proceeds to decision point 232 where a determination is made is $TW < LL$. If the answer is "yes" the program branches to block 234 where the insufficient indicator light 50 in the controller 22 is turned on to indicate that the weight of the sample plus the diluent for achieving the previously set dilution factor f is less than the specified minimum weight which has been set with the minimum weight control 55. The program then proceeds to block 236 where the memory elements in the controller 22 are reset with switch 28 to prepare the system for another dilution. The program then proceeds to stopping point 238 which terminates all activity in the program. If the answer is "no" at decision point 232 the program proceeds to block 240 where the pump 42 is turned on and the valve 34 opened. At this point, the pump is pumping diluent 36 into the container at the higher rate of flow permitted by valve 34 than is possible with valve 46. The program then proceeds to block 242 where the BCD output from scale 12 of the combined weight of diluent and sample is read. The program then proceeds to decision point 244 where a determination is made if $TW - W \leq 10$. If the answer is "no" the program loops back to block 242 and to decision point 244 where the calculation $TW - W \leq 10$ is made. As long as $TW - W > 10$, valve number 34 is open and the highest flow rate of diluent into the container 20 takes place. The program continues to loop until TW−W=10 at which point the program branches to block 246 where valve 34 is closed and valve 46 is opened. At this point the flow rate into the container 20 has been reduced by a factor of 10 as a consequence of the lower rated flow capacity of valve 46 in comparison with valve 34. The program then proceeds to block 248 where the weight W of sample plus diluent is read from the scale 12. The program then proceeds to decision point 250 where a determination is made if TW−W≦1. If the answer is "no," the program loops back to block 248. If the answer is "yes," the program proceeds to block 252 where the valve is pulsed to be on for 0.2 seconds and pulsed off for 1.8 seconds. The program proceeds to block 254 where the weight of the sample plus diluent is read from scale 12. The program then proceeds to decision point 256 where a determination is made if TW=W. If the answer is "no," the program loops back to block 252 where the valve 46 is again pulsed. The program continues to loop until TW=W at which time the program proceeds to block 258 where valve 46 is closed and valve 34 is maintained in its previously closed state. At this point in time, the predetermined weight dilution factor f of diluent has been achieved and the combined weight of sample plus diluent equals TW. The program then proceeds to block 260 where pump 42 is turned off, the ready light in the controller 22 is lit and the memory elements of the controller are reset. The program then proceeds to stopping point 262 where no further program action occurs.

Figure 4:
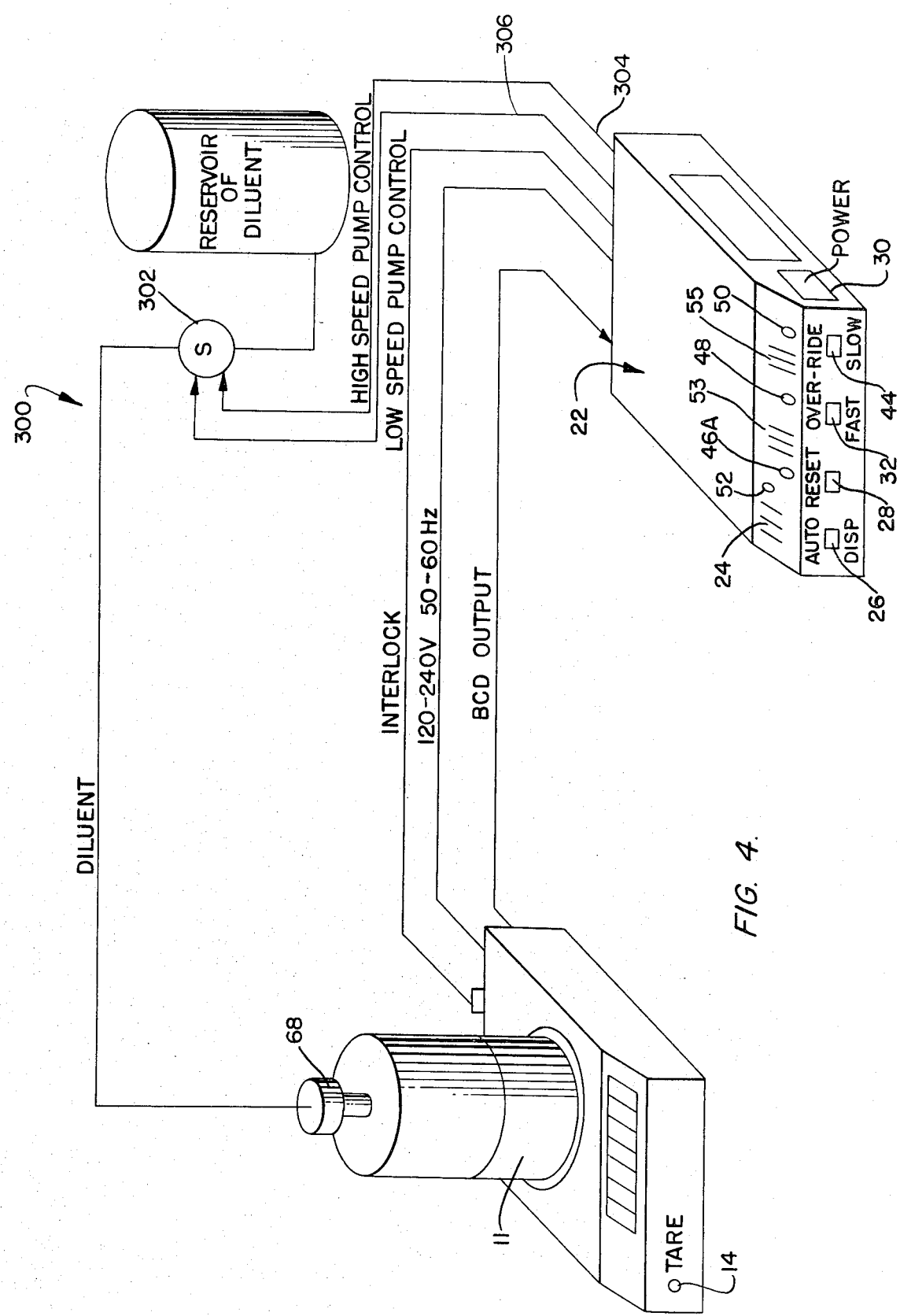
FIG. 4 is a system schematic of another embodiment of the present invention.

FIG. 4 is a general system schematic of the second embodiment 300 of the present invention. The second embodiment is identical to the first embodiment of the present invention which is illustrated in FIG. 1 with the exception that the apparatus for controlling the flow of diluent is different. Identical parts in FIGS. 1 and 4 are identified by identical reference numerals. In the second embodiment of the invention, the flow of diluent between the reservoir and the container is controlled by the starting and stopping of a pump 302 without the first and second valves 34 and 46 of FIG. 1. The pump may be any type of pump which stops the pumping of fluid immediately when a stop command is applied thereto on lines 304 and/or 306 from controller 22. There are many types of pumps which have this capability. The preferred type of a pump is a peristaltic pump which may be a model Master Flex Pump C-7500-00 manufactured by the Cole-Parmer Corporation of Chicago, Ill. The peristaltic pump is preferred because it may be controlled to immediately cease the pumping of fluid. The present invention requires the immediate ceasing of fluid flow into container 20 when TW−W=0 in order to acheive accurate dilutions which are very close to the predetermined dilution factor f. In this embodiment, reciprocating pumps, centrifugal pumps, rotary pumps, or other types of pumps which have a relatively high inertia during pumping would not be useful unless they contained valving which permitted the immediate stopping of the flow of liquid upon the application of the stop command from the controller 22. Without valving to immediately stop the flow of diluent, the inertia of the operating pump would result in the continued pumping of diluent after the application of the stop command which would result in a dilution to a greater dilution factor than the factor f.

The second embodiment may include a pump 302 which may be controlled to pump at two different flow rates which are used such that the higher flow rate is used when the quantity TW−W>10 and the lower flow rate is used when 0<TW−W<10 in a manner analogous to the two valve mechanisms of the first embodiment.

A control system like the one which is illustrated in FIG. 2 and a microprocessor flow chart like the one illustrated in FIG. 3 may be used with the second embodiment. The only difference between the control system of FIG. 2 and the microprocessor flow chart of FIG. 3 for the first embodiment and the control system and microprocessor flow chart of the second embodiment is that in the second embodiment the valves 34 and 46 are omitted and the signals for controlling the flow of diluent are applied directly to the pump 302.

Operation

The operation of the invention to make a dilution of a sample of ethanol with a 50% solution by weight (f=0.5) of water is summarized as follows. The maximum and minimum weights UL and LL have been previously set by the maximum and minimum weight controls 53 and 55 of the controller 22 and are assumed to not warrant system shutdown. The dilution factor f is set at 0.5 by the dilution factor selector control 24. The TARE control 14 is activated to zero the BCD output of the scale 12 after the container 20 has been placed on the pan 18. The sample of ethanol is then placed in the container 20 and the automatic dispenser switch 26 is depressed. The BCD output from the scale specifies that the sample is 100 grams. The means for calculating TW:

$$\frac{\text{weight of sample}}{f} = \frac{100 \text{ grams}}{0.5} = 200 \text{ grams}$$

reflects that the combined weight of ethanol and water to achieve an 0.5 dilution factor is 200 grams. The pump 42 is immediately activated and rapid dispense valve 34 is opened. The pump then proceeds to pump water into the container 20 through valve 34 until the combined weight of the water plus ethanol reaches 190 grams at which point the program causes rapid dispense valve 34 to close and slow dispense valve 46 is opened to reduce the rate of introduction of water into the container 20. When the weight of ethanol plus water W equals 199 grams, the valve 46 is repeatedly pulsed on for 0.2 seconds and off for 1.8 seconds. The pump 42 continues to pump water into the container through the pulsating valve 46 until the weight of the water plus ethanol equals 200 grams which is equal to the previously calculated TW. The pump 42 is then shut off and valve 46 is closed to complete the dilution.

Although the present invention has been described with reference to two particular embodiments, it should be understood that those skilled in the art may make many other modifications without departing from the spirit and scope of the invention as defined by the appended claims. For example, the invention is not limited to the particular disclosed values of the quantity TW−W which control the activation of valves 34 and 46 or the pump 302. Moreover, the particular apparatus for calculating various quantities does not form part of the invention since any well known calculating apparatus may be used.

What is claimed as new and desired to be secured by patent of the United States is:

1. An apparatus for diluting a sample within a container to a dilution factor f by weight of diluent comprising:
   (a) means for repeatedly measuring the weight W of the sample plus any diluent within the container;
   (b) means for choosing a dilution factor f by weight of a diluent to be used for diluting the sample;
   (c) means for calculating TW wherein $TW = W/f$ and W is the weight of the sample within the container prior to the addition of diluent;
   (d) means for calculating $TW - W$;
   (e) fluid conducting means disposed between a reservoir of diluent and the container for permitting the diluent to flow from the reservoir to the container for the purpose of diluting the sample within the container to the selected dilution factor f; and
   (f) means responsive to the means for calculating $TW - W$ for controlling the flow of diluent between the reservoir and the container to cause diluent to flow between the container and the reservoir when $TW > W$ and to stop the flow of diluent when $TW = W$.

2. The apparatus of claim 1 wherein the means responsive to the means for calculating is a pump.

3. The apparatus of claim 2 wherein the pump is a peristalic pump.

4. The apparatus of claim 1 further comprising:
   (a) means for calculating when $TW - W = C$ where C is a predetermined weight and wherein
   (b) the means for controlling maintains a higher flow rate when $TW - W > C$ and a lesser rate of flow when $TW - W \leq C$.

5. The apparatus of claim 4 wherein the means for controlling is a pump having two specified rates of flow, the pump pumping at the higher rate when $TW - W > C$ and at the lower rate when $TW - W > C$.

6. The apparatus of claim 5 wherein the pump is a peristaltic pump.

7. An apparatus for diluting a sample within a container to a dilution factor f by weight of diluent comprising:
   (a) means for repeatedly measuring the weight W of the sample plus any diluent within the container;
   (b) means for choosing a dilution factor f by weight of a diluent to be used for diluting the sample;
   (c) means for calculating TW wherein $TW = W/f$ and W is the weight of the sample within the container prior to flow the addition of diluent;
   (d) means for comparing TW and W;
   (e) fluid conducting means disposed between a reservoir of diluent and the container for permitting the diluent to from the reservoir to the container for the purpose of diluting the sample within the container to the selected dilution factor f; and
   (f) means responsive to the means for comparing TW and W for controlling the flow of diluent between the reservoir and the container to cause diluent to flow between the container and the reservoir when $TW > W$ and to stop the flow of diluent when $TW = W$.

* * * * *